(12) United States Patent
Rivier

(10) Patent No.: US 12,364,848 B2
(45) Date of Patent: Jul. 22, 2025

(54) ADAPTOR FOR MOUNTING ONTO A MEDICAL CONTAINER, A MEDICAL CONTAINER COMPRISING SAID ADAPTOR, AND A DRUG DELIVERY DEVICE COMPRISING SAID MEDICAL CONTAINER

(71) Applicant: Becton Dickinson France, Le Pont-de-Claix (FR)

(72) Inventor: Cédric Rivier, Voreppe (FR)

(73) Assignee: Becton Dickinson France, Le Pont-de-Claix (FR)

( * ) Notice: Subject to any disclaimer, the term of this patent is extended or adjusted under 35 U.S.C. 154(b) by 399 days.

(21) Appl. No.: 17/800,368

(22) PCT Filed: Feb. 17, 2021

(86) PCT No.: PCT/EP2021/053851
§ 371 (c)(1),
(2) Date: Aug. 17, 2022

(87) PCT Pub. No.: WO2021/165297
PCT Pub. Date: Aug. 26, 2021

(65) Prior Publication Data
US 2023/0073350 A1 Mar. 9, 2023

(30) Foreign Application Priority Data
Feb. 18, 2020 (EP) ..................................... 20305154

(51) Int. Cl.
*A61M 39/10* (2006.01)
*A61J 1/20* (2006.01)
*A61M 5/34* (2006.01)

(52) U.S. Cl.
CPC ............ *A61M 39/10* (2013.01); *A61J 1/2055* (2015.05); *A61J 1/2096* (2013.01); *A61M 5/345* (2013.01); *A61M 2039/1077* (2013.01)

(58) Field of Classification Search
CPC ................. A61M 39/10; A61M 5/345; A61M 2039/1077; A61M 2039/1044;
(Continued)

(56) References Cited

U.S. PATENT DOCUMENTS 3,897,090 A * 7/1975 Maroschak ........... F16L 37/084
285/260
4,758,023 A * 7/1988 Vermillion ............. F16L 11/111
285/903
(Continued)

FOREIGN PATENT DOCUMENTS

JP H9154947 A 6/1997
JP 2008119359 A 5/2008
(Continued)

Primary Examiner — Ariana Zimbouski
Assistant Examiner — Alessandro R Del Priore
(74) Attorney, Agent, or Firm — The Webb Law Firm

(57) ABSTRACT

The adaptor includes a tubular wall having a proximal part configured to be secured onto a distal tip of a medical container and a distal part configured to receive said connector. The adaptor further includes an opening extending through said tubular wall, and an inner thread configured to cooperate with a connection element of the connector in order to secure the connector to the adaptor. The inner thread is configured to guide the connection element into said opening. The opening is positioned relative to the inner thread so as to make the connection element be visible to an end user when the connection between the adaptor and the connector is completed.

17 Claims, 4 Drawing Sheets

(58) Field of Classification Search
CPC .. A61M 39/1011; A61M 5/344; A61J 1/2055; A61J 1/2096; F16L 2201/10; F16L 2201/60; F16L 2201/44; F16L 2201/00
See application file for complete search history.

(56) References Cited

U.S. PATENT DOCUMENTS

| | | | | |
|---|---|---|---|---|
| 5,071,413 | A * | 12/1991 | Utterberg | A61M 5/162 604/905 |
| 5,591,143 | A * | 1/1997 | Trombley, III | A61M 39/10 604/905 |
| 6,152,913 | A * | 11/2000 | Feith | A61M 39/1011 604/533 |
| 6,817,632 | B1 * | 11/2004 | You | F16L 25/0063 285/903 |
| 7,814,827 | B2 * | 10/2010 | Frenken | B25B 27/10 100/102 |
| 7,837,237 | B2 * | 11/2010 | Passlack | F16L 37/252 285/361 |
| 10,933,228 | B2 | 3/2021 | Hallynck et al. | |
| 2006/0178627 | A1 | 8/2006 | Geiger et al. | |
| 2008/0178627 | A1 | 7/2008 | Jang et al. | |
| 2008/0188816 | A1 | 8/2008 | Shimazaki et al. | |
| 2020/0022870 | A1 | 1/2020 | Barrelle et al. | |

FOREIGN PATENT DOCUMENTS

| | | | |
|---|---|---|---|
| JP | 2016525003 A | 8/2016 | |
| WO | 2011068544 A1 | 6/2011 | |

* cited by examiner

ADAPTOR FOR MOUNTING ONTO A MEDICAL CONTAINER, A MEDICAL CONTAINER COMPRISING SAID ADAPTOR, AND A DRUG DELIVERY DEVICE COMPRISING SAID MEDICAL CONTAINER

CROSS-REFERENCE TO RELATED APPLICATIONS

This application is the United States national phase of International Application No. PCT/EP2021/053851 filed Feb. 17, 2021, and claims priority to European Patent Application No. 20305154.5 filed Feb. 18, 2020, the disclosures of which are hereby incorporated by reference in their entirety.

BACKGROUND OF THE DISCLOSURE

Field of the Disclosure

The present disclosure relates to an adaptor for mounting onto a medical container, a medical container comprising said adaptor, and a drug delivery device comprising said medical container.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to an adaptor or a medical container of the invention, and the "proximal direction" is to be understood as meaning the opposite direction to said direction of injection, that is to say the direction towards the user's hand holding a medical container as for an injection operation.

Basically, medical containers, such as for example syringes, are preferably made of glass for its high chemical passivity, its low gas permeability and high transparency, which allows an extended storage and an easy inspection.

The medical container usually comprise a container forming a reservoir for containing a medical product. The container has a distal end in the form of a longitudinal tip defining an axial passageway through which the medical product is expelled from the container. However, this longitudinal tip does not allow parenteral administration by itself and must either comprise a staked needle or an adaptor allowing the connection of the syringe to a connector such as a needle hub. This connector is typically screwed into the adaptor and engages the distal end of the container to establish a fluid path between the reservoir and said connector.

Description of Related Art

It is important that the connector be properly screwed into the adaptor. The end user has to apply a sufficient torque when screwing the connector into the adaptor in order to get a proper fitting of the connector onto the distal end of the container. Under-screwing or over-screwing of the connector into the adaptor may otherwise lead to a leakage or an ejection of the connector due to internal pressure when transferring a fluid between the container and the connector.

There is therefore a need for a medical container providing the end user with an indication that the connector is properly screwed into the adaptor and thus improving the end user confidence during a connection and an injection step.

The document US2006178627 discloses a syringe tip cap for closing a distal opening of a syringe body. The document WO2011068544 discloses a cartridge for containing and dispensing a medicament in conjunction with a pen injection device. The document US2020022870 discloses an adaptor for coupling to a vial, said adaptor allowing for multiple aseptic needle piercings with an injection device to be filled with the product contained in the vial.

SUMMARY OF THE DISCLOSURE

An aspect of the disclosure is an adaptor for connecting a medical container to a connector, the adaptor comprising a tubular wall having
  a proximal part configured to be secured onto a distal tip of a medical container,
  a distal part configured to receive said connector, wherein the adaptor further comprises
  at least one opening extending through said tubular wall, and
  an inner thread configured to cooperate with a connection element of the connector in order to secure the connector to the adaptor, wherein
  said inner thread is configured to guide the connection element into said at least one opening, and wherein
  said at least one opening is positioned relative to the inner thread so as to make the connection element be visible to an end user when the connection between the adaptor and the connector is completed. Consequently, the adaptor provides a visual indication that the connection is completed.

The adaptor of the invention thus provides a visual indication that the connector is safely and sufficiently screwed into the adaptor. This prevents either over- or under-screwing of the connector into the adaptor.

In an embodiment, the tubular wall has an inner surface configured to exert a radial inward force onto the connection element of the connector when the connector is screwed into the adaptor.

This causes the connection element to hit a wall of the opening and produce a sound when entering the opening. As a result, the adaptor may further provide an audible indication that the connection is completed.

Preferably, the inner surface of the tubular wall comprises a tapered portion.

The tapered inner surface thus causes a progressive compression of the connection element, thereby avoiding a sharp increase of the screwing torque. This also permits that the connector be uniformly stressed when screwed into the adaptor, thereby improving reliability of the connection.

Preferably, the at least one opening extends at least partly through said inner surface, preferably through said tapered portion.

In an embodiment, the at least one opening is located in a thread root of the inner thread.

This improves the reliability of the connection.

In an embodiment, the at least one opening is configured to accommodate the connection element.

Therefore, the opening helps maintain the connector fixed relative to the adaptor, thereby preventing a further screwing or a withdrawal of the connector. This permits to benefit from the advantage of both a screwing and a snap-fit connection.

The adaptor advantageously comprises at least two openings. The end user thus does not have to rotate the adaptor in order to visually check that the connection is completed.

Preferably, the two or more openings are regularly distributed in a circumferential direction. This avoids an asymmetric deformation of the connector.

In an embodiment, the adaptor is configured to be glued, clipped or snap-fitted onto the distal tip of the medical container.

In an embodiment, the adaptor is made of a light-transmitting material.

This enhances the visual indication provided by the connection element engaged in the opening.

The adaptor may be injection molded.

Another aspect of the invention is a medical container comprising a distal tip and the above-described adaptor, said adaptor being secured to the distal tip.

In an embodiment, an inner surface of the adaptor and an outer surface of the distal tip define a cavity configured to receive the connector, said cavity having a proximally decreasing cross section.

This increases the radial pressure exerted by the inner surface of the adaptor onto the connection element, thereby improving the audible indication provided to the end user.

The distal tip may have a cylindrical or a frustoconical shape.

In an embodiment, the distal tip has a frustoconical shape.

The adaptor may be glued, clipped or snap-fitted onto the distal tip.

The medical container may be made of a glass or plastic material.

Another aspect is a drug delivery device comprising the above-described medical container and a connector configured to be secured to the adaptor.

The connector may be a needle hub.

In an embodiment, the at least one opening and the connection element are complementarily shaped.

Therefore, the opening and the connection element achieve both a screwing and snap-fit connection.

In an embodiment, the connection element is configured to hit a wall of the opening when reaching the opening.

For instance, the connection element may hit an inner edge of the opening or the distal and/or proximal abutment surfaces of said opening.

The adaptor may comprise several openings and the connector may comprise several connection elements, each of said connection elements being received in a corresponding opening of the adaptor. This accordingly avoids an asymmetric deformation of the connector. The openings, respectively the connection elements, may be regularly distributed in a circumferential direction.

Typically, the adaptor comprises two openings and the connector comprises two connection elements such as outer wings.

In an embodiment, the adaptor comprises a first shade and the connection element comprises a second shade that is different from said first shade.

The adaptor may comprise polycarbonate (PC), while the connector may comprise polypropylene (PP).

BRIEF DESCRIPTION OF THE DRAWINGS

The disclosure and the advantages arising therefrom will clearly emerge from the detailed description that is given below with reference to the appended drawings as follows.

DESCRIPTION OF THE INVENTION

Figure 1:
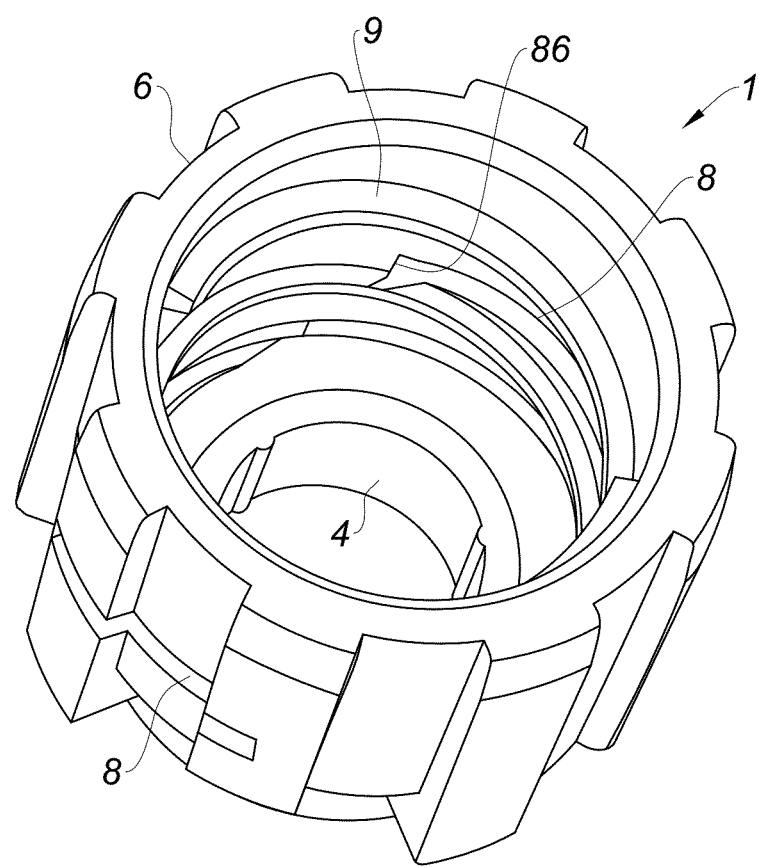
FIG. 1 is a perspective view of an adaptor according an embodiment of the invention.
Figure 4:
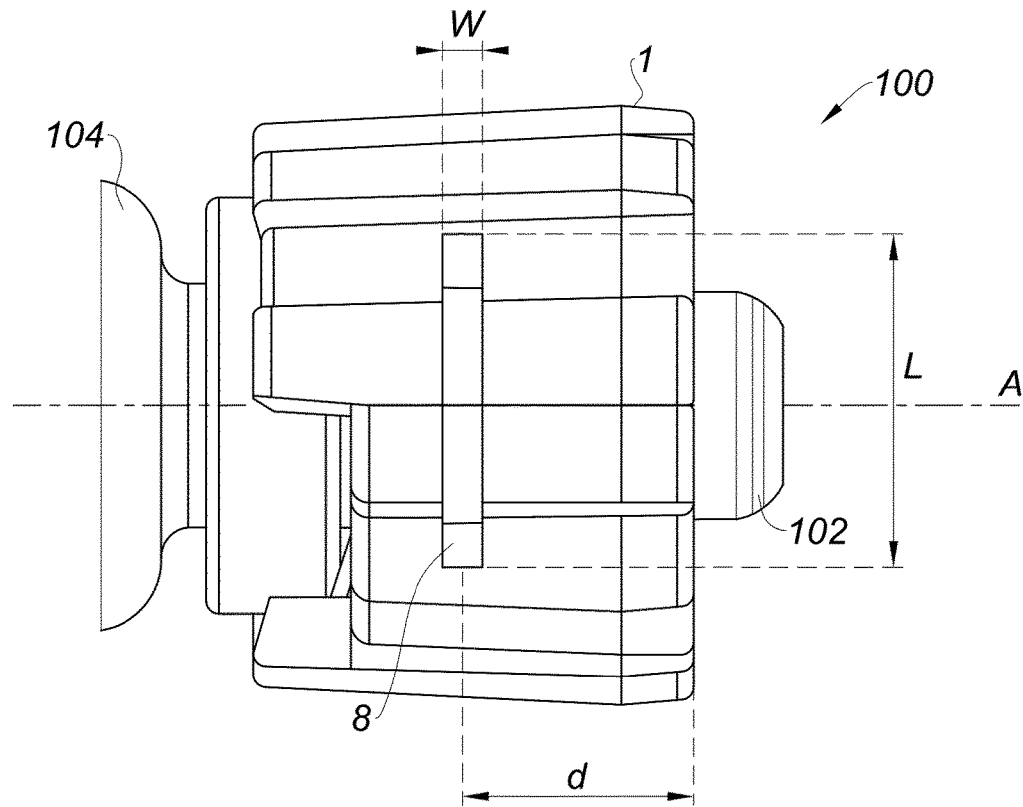
FIG. 4 is a side view of an adaptor and a medical container according an embodiment of the invention.

With reference to FIG. 1 is shown an adaptor 1 according to an embodiment of the disclosure. With reference to FIG. 4, the adaptor 1 is intended to be mounted onto a distal tip 102 of a medical container 100, more precisely onto an outer surface of said distal tip 102. The outer surface may be either cylindrical or distally tapered. The distal tip 102 extends in a longitudinal direction A. As shown on FIG. 5, the adaptor 1 permits to connect a connector, more specifically a needle hub 200, to this distal tip 102. The connector is provided with a connection element, such as outer wings 202, in order to secure the connector to the adaptor 1.

Figure 2:
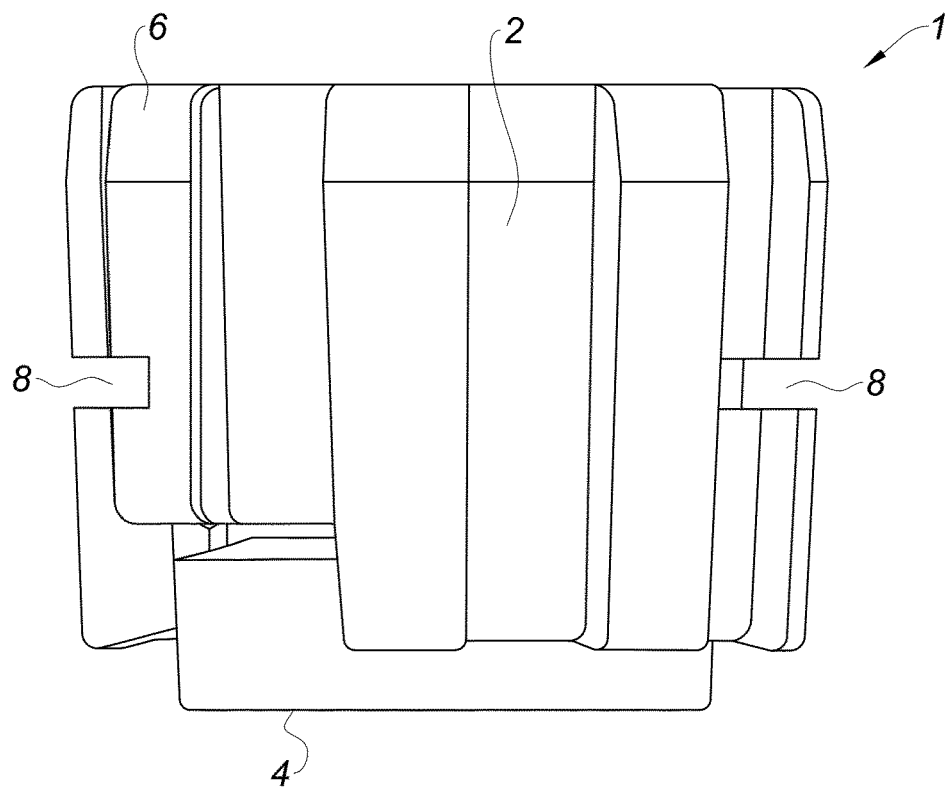
FIG. 2 is a side view of an adaptor according an embodiment of the invention.
Figure 3:
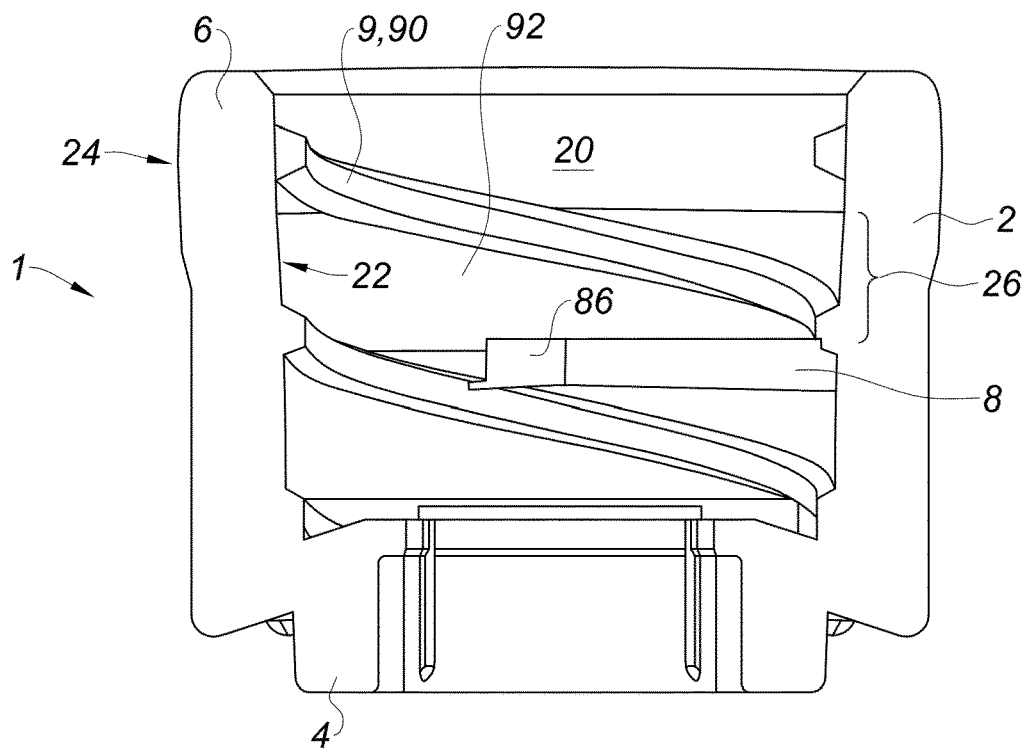
FIG. 3 is a cross section view of an adaptor according an embodiment of the invention.

With reference to FIGS. 1-3, the adaptor 1 comprises a cylindrical body in the form of a tubular wall 2 defining an inner cavity 20. The adaptor 1 defines a proximal part 4, which may be in the form of a mounting ring, configured to be secured to the medical container 100, and a distal part 6, which may be in the form of a connecting ring, configured to receive the connector in order to establish a reliable fluid communication between a passageway of the distal tip 102 and said connector.

The tubular wall 2 has an inner surface 22 and an outer surface 24. The tubular wall 2 is provided with one or several through, for example two, openings 8 configured to cooperate with the connection element(s) of the connector in order to provide the end user with a visual indication that the connection between the connector and the adaptor 1 is completed. In the example shown, the tubular wall 2 comprises two openings 8, since the needle hub 200 comprises two outer wings 202. Each of these opening 8 is configured to cooperate with a corresponding one of said outer wings 202. The openings 8 may be regularly distributed in a circumferential direction. The two openings 8 shown on FIGS. 1 to 7 are accordingly diametrically opposite.

The one or several openings 8 extend from the inner surface 22 to the outer surface 24 of the tubular wall 2 in a preferably straight radial direction, thereby providing an end user with a visibility of the inner cavity 20. As visible on FIG. 2 or 4, the one or several openings 8 may also extend in a plane orthogonal to the longitudinal axis A, thereby being inclined relative to the inner thread 9.

With reference to FIG. 3, the adaptor 1, more specifically the distal part 6, further comprises an inner thread 9 protruding from the inner surface 22. The inner thread 9 defines a thread crest 90 and a thread root 92. The inner thread 9 is configured to cooperate with the outer wings 202 of the needle hub 200 in order to secure the needle hub 200 to the adaptor 1. The inner thread 9 is also configured to guide the outer wings 202 towards the opening 8 so as to make the outer wings 202 become visible to the end user as soon as the connection between the needle hub 200 and the adaptor 1 is completed. The one or several openings 8 are arranged on the path of the connection element(s) when the connector is screwed into the adaptor 1. More specifically, the one or more openings 8 extend in the tread root 92 of the inner thread 9. The one or more openings 8 may also have one end in a circumferential direction that is adjacent to or extends through the thread crest 90 of the inner thread 9, more specifically at a distal side of said thread crest 90 as illustrated on FIG. 3.

The one or several openings 8 are within the adaptor 1 so that the outer wings 202 become visible to the end user only when the connection between the needle hub 200 and the adaptor 1 is safe and completed. This substantially corresponds to a predetermined position wherein the needle hub 200 properly fits with the distal tip 102 of the medical container 100, as shown on FIGS. 5 to 7. Said predetermined position is advantageously defined as being the leakage limit of the needle hub 200 as defined in the ISO 80369-7 (2016) (paragraphs 6.1 and 6.2). Whether the needle hub 200 is under connected and has not reach said position, a leakage may occur. On the contrary, if the needle hub 200 has been over connected, the needle hub 200 may be broken or ejected from the adaptor. It should be noted that the one or several openings 8 are configured to accommodate the connection element, i.e. the outer wing 202, only when the needle hub 200 reaches the leakage limit position.

As shown on FIG. 3, the one or several openings 8 may be located at at least one screw pitch from a distal end of the innerthread 9, so that the outer wings 202 reach the openings 8 after at least one 360° revolution around the longitudinal axis A.

With reference to FIG. 4, the one or more openings 8 may be located at a distance d from the distal end of the adaptor 1, said distance d for example being at least equal to 2 mm and preferably being no more than 6 mm. The one or more openings 8 may have a width w that may be at least equal to 0.5 mm and preferably no more than 1 mm. The one or more openings 8 may have an arc length L that may be at least equal to 5 mm and preferably no more than 7 mm.

It should be noted that the inner surface 22 may be configured to exert a radial inward force onto the outer wings 202 when the needle hub 200 is screwed into the adaptor 1. For example, the inner surface 22 may comprise a proximally tapered portion 26 that delimits a decreasing cross section in a proximal direction. The tapered portion 26 may have a frustoconical shape. The opening 8 may be proximally located relative to said portion 26, or may be arranged through said portion 26 of the inner surface 22, preferably at the proximal end of the portion 26. As a result, the outer wings 202 resiliently deform when the needle hub 200 is screwed into the adaptor 1. The one or several openings 8 then release the outer wings 202 that hit a wall of the opening 8, thereby providing the end user with an audible indication that the connection is completed. The inner surface 22 may further comprise a cylindrical portion proximally and/or distally relative to the tapered portion 26. Although not shown on the figures, the inner surface 22 may alternatively be completely cylindrical and exert a reacting force against the outer wings 202, said outer wings 202 being pressed against the inner surface 22 by the distal tip 102 having a frustoconical shape when the needle hub 200 is screwed into the adaptor 1.

When the inner surface 22 comprises the tapered portion 26, it is contemplated that only the thread root 92 of the inner thread 9 tapers. The thread crest 90 however has a substantially cylindrical shape. That is, the thread crest 90 still defines a constant diameter while the diameter of the conduit defined by the inner surface proximally decreases.

The one or more openings 8 are configured to accommodate the corresponding outer wings 202 in order to achieve a snap-fit connection in addition to the screwing connection achieved by the inner thread 9 and the outer wings 202. As a result, the resiliently deformed outer wings 202 pop out into the openings 8 when the connection is safe.

Figure 6:
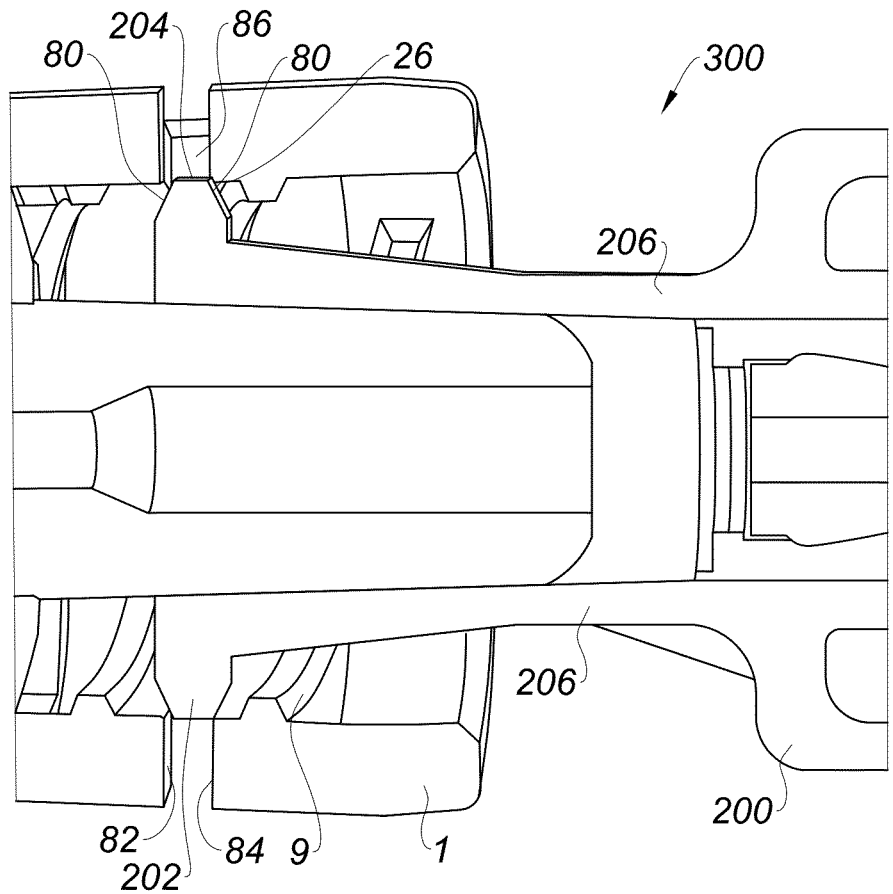
FIG. 6 is a cross section view of an adaptor and a drug delivery device according an embodiment of the invention.
Figure 7:
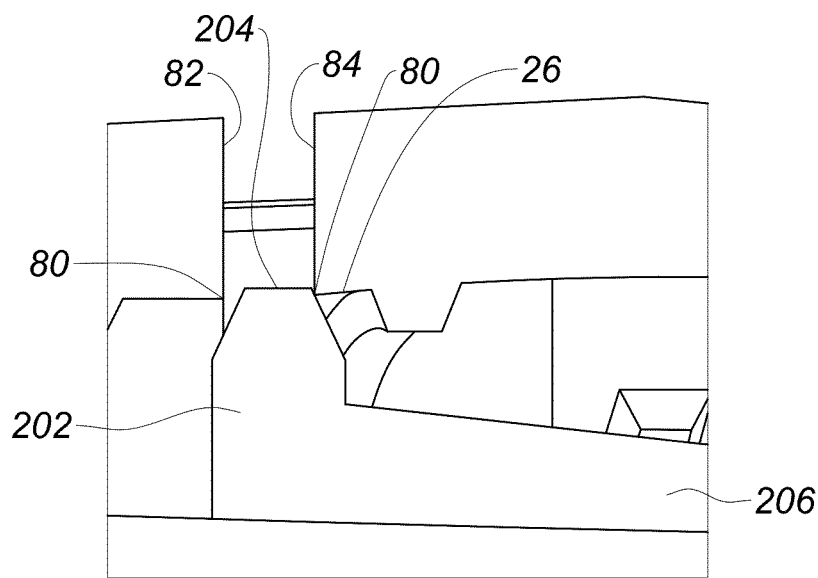
FIG. 7 is a detail of FIG. 6.

More specifically, the one or more openings 8 and the outer wings 202 may be complementarily shaped, so that the outer wings 202 engage the openings 8 and remain trapped inside said openings 8. With reference to FIGS. 6 and 7, the outer wings 202 may have a free end 204 configured to at least partially enters the openings 8. Said free end 204 may have a tapered shape in an outward radial direction. The free end 204 may thus hit the adaptor 1 at inner edges 80 of the openings 8. The one or more openings 8 may define a proximal and a distal abutment surfaces 82, 84 blocking the outer wings 202 in the longitudinal direction A. The one or more openings 8 may also have orthoradial abutment surfaces 86 in order to block the outer wings 202 in a circumferential direction, thereby preventing any further or reverse screwing of the needle hub 200 into the adaptor 1.

The adaptor 1 may be preferably glued onto the distal tip 102 of the medical container 100. Therefore, the proximal part 4 of the adaptor 1 may comprise an accommodation space configured to receive a glue material.

The adaptor 1 may be made of a plastic material, more precisely of any rigid polymer adapted to medical use, such as high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and combinations thereof. Preferably, the adaptor 1 is made of polycarbonate (PC). The adaptor 1 is preferably made of a light-transmitting material. The adaptor 1 may be injection molded.

With reference to FIG. 4, the invention also relates to a medical container 100 comprising a distal tip 102 and the above-described adaptor 1, said adaptor 1 being mounted onto the distal tip 102, for example by gluing. The medical container may be made of a glass. Preferably, the medical container is a syringe, such as a pre-filed or pre-fillable syringe. The medical container 100 comprises a tubular barrel 104 that defines a reservoir for a medical product. The distal tip 102 may be cylindrical or distally tapered.

Due to the conical portion 26 of the inner surface 22 and/or the conical shape of the distal tip 102, the inner cavity 20 has a proximally decreasing cross section. Therefore, the inner surface 22 exerts a radial force on the outer wings 202 that are resiliently deformed. The outer wings 202 move back towards their original shape from the moment that they reach the openings 8, thereby producing a sound indicating the connection completion.

Figure 5:
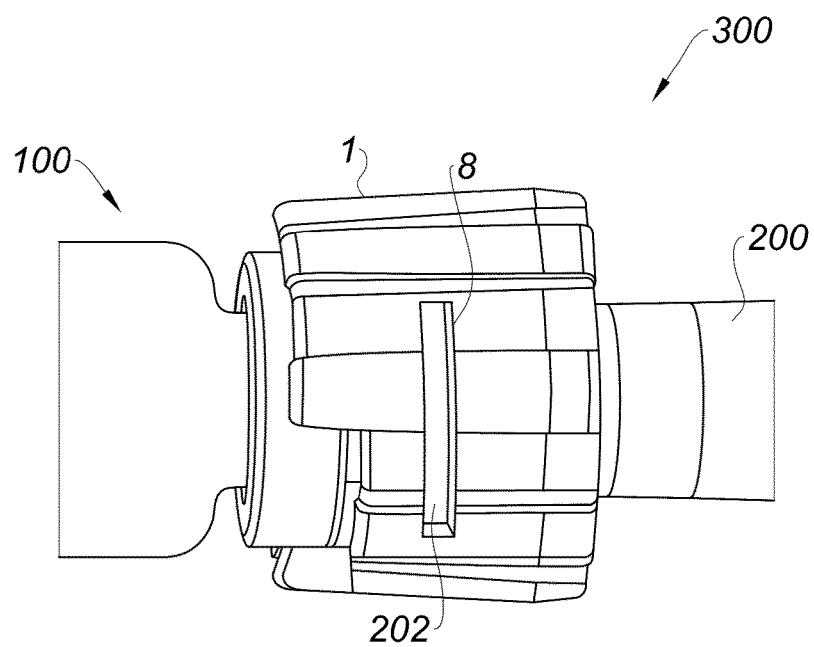
FIG. 5 is a side view of an adaptor and a drug delivery device according an embodiment of the invention.

With reference to FIGS. 5 and 6, the invention also relates to a drug delivery device 300 comprising the above-described medical container 100 and a connector, such as a needle hub 200, secured to the adaptor 1. The needle hub 200 has an open proximal end for receiving the distal tip 102, a needle cannula, and resilient arms 206, said resilient arms 206 having an end provided with an outer wing 202.

The adaptor 1 of the drug delivery device 300 may comprise as many openings as the outer wings 202 of the needle hub 200. Each of the outer wings 202 cooperate with one of the openings 8. The openings 8, respectively the outer wings 202, may be regularly distributed in a circumferential direction.

The adaptor 1 may advantageously comprise a a first shade while the needle hub 200 comprises a second shade that is different from said first shade. The first shade may be a light transmitting material while the second shade may be a more opaque material than said first shade. Alternatively, the first shade may be a first color or color shade, the second shade being of a different color or color shade.

The adaptor 1 may be made of polycarbonate (PC) and the needle hub 200 may be made of polypropylene (PP).

The invention claimed is:

1. An adaptor for connecting a medical container to a connector, the adaptor comprising a tubular wall,
   wherein the tubular wall comprises:
   a proximal part configured to be secured onto a distal tip of a medical container,
   a distal part configured to receive said connector, and
   an inner surface comprising a tapered portion,
   wherein the adaptor further comprises:
   at least one opening located proximate to the tapered portion of the inner surface and extending through said tubular wall, and
   an inner thread configured to cooperate with a connection element of the connector, in order to secure the connector to the adaptor,
   wherein the inner thread defines a thread crest and a thread root,
   wherein said inner thread is configured to guide the connection element into said at least one opening, and
   wherein said at least one opening is positioned relative to the inner thread so as to make the connection element be visible to an end user when the connector reaches a leakage limit position wherein the connection between the adaptor and the connector is completed,
   wherein the at least one opening extends through at least a portion of the thread crest, and
   wherein at least the tapered portion of the inner surface of the tubular wall is configured to exert a radial inward force onto the connection element of the connector when the connector is screwed into the adaptor.

2. The adaptor according to claim 1, wherein the opening extends at least partly through said inner surface.

3. The adaptor according to claim 1, wherein the opening is located in a thread root of the inner thread.

4. The adaptor according to claim 1, wherein the opening is configured to accommodate the connection element.

5. The adaptor according to claim 1, wherein the adaptor is configured to be glued, clipped or snap-fitted onto the distal tip of the medical container.

6. The adaptor according to claim 1, wherein the adaptor is made of a light-transmitting material.

7. A medical container comprising a distal tip and an adaptor according to claim 1, said adaptor being secured to the distal tip.

8. A medical container according to claim 7, wherein an inner surface of the adaptor and an outer surface of the distal tip define a cavity configured to receive the connector, said cavity having a proximally decreasing cross section.

9. A medical container according to claim 7, wherein the distal tip has a frustoconical shape.

10. A drug delivery device comprising a medical container according to claim 7, and a connector configured to be secured to the adaptor.

11. A drug delivery device according to claim 10, wherein the opening and the connection element are complementarily shaped.

12. A drug delivery device according to claim 10, wherein the connection element is configured to hit a wall of the opening when reaching said opening.

13. A drug delivery device according to claim 10, wherein the adaptor comprises a first shade and the connection element comprises a second shade that is different from said first shade.

14. The drug delivery device according to claim 1, wherein the at least one opening extends from the at least a portion of the thread crest in a distal direction.

15. The drug delivery device according to claim 1, wherein the at least one opening through at least a portion of the thread root.

16. The drug delivery device according to claim 1, wherein along the tapered portion, the thread crest defines a constant diameter and the thread root is tapered.

17. The drug delivery device according to claim 1, wherein the at least one opening is inclined relative to the inner thread.

* * * * *